United States Patent [19]

Finney

[11] 4,212,304
[45] Jul. 15, 1980

[54] URETHERAL CATHETER STENT

[75] Inventor: Roy P. Finney, Tampa, Fla.

[73] Assignee: Medical Engineering Corp., Racine, Wis.

[21] Appl. No.: 894,278

[22] Filed: Apr. 7, 1978

[51] Int. Cl.² ............................................ A61M 25/00
[52] U.S. Cl. ............................................... 128/349 R
[58] Field of Search .............. 128/221, 242, 294, 341, 128/343, 348, 349 R, 350 R

[56] References Cited

U.S. PATENT DOCUMENTS

| | | | |
|---|---|---|---|
| 2,212,334 | 8/1940 | Wallerich | 128/349 R |
| 2,857,915 | 10/1958 | Sheridan | 128/349 R |
| 3,419,010 | 12/1968 | Williamson | 128/350 R |
| 3,726,269 | 4/1973 | Webster, Jr. | 128/348 |
| 3,890,977 | 6/1975 | Wilson | 128/350 R |
| 3,920,023 | 11/1975 | Dye et al. | 128/350 R |
| 3,938,529 | 2/1976 | Gibbons | 128/349 R |

OTHER PUBLICATIONS

"Ureteral Indwelling Pigtail Stent Set", Cook, Inc.
"Indwelling Ureteral Stent", Heyer-Schulte Corp., 1974.

Primary Examiner—Robert W. Michell
Assistant Examiner—C. F. Rosenbaum

[57] ABSTRACT

An ureteral catheter stent comprises an elongated, flexible tubular member of uniform outside diameter throughout its length which has proximal and distal ends which are in the form of hooks. Openings extend through the wall of the member to provide passages for fluid to enter the lumen of the tubular member and the proximal end of the member is closed to facilitate its introduction into a body passage. Since the stent is straightened for introduction into a body passage by inserting a wire stylet in the lumen of the stent, the stent is provided with indicating means which show the direction the proximal hook will form when the stylet is removed so that proper placement is insured.

14 Claims, 4 Drawing Figures

U.S. Patent  Jul. 15, 1980  4,212,304
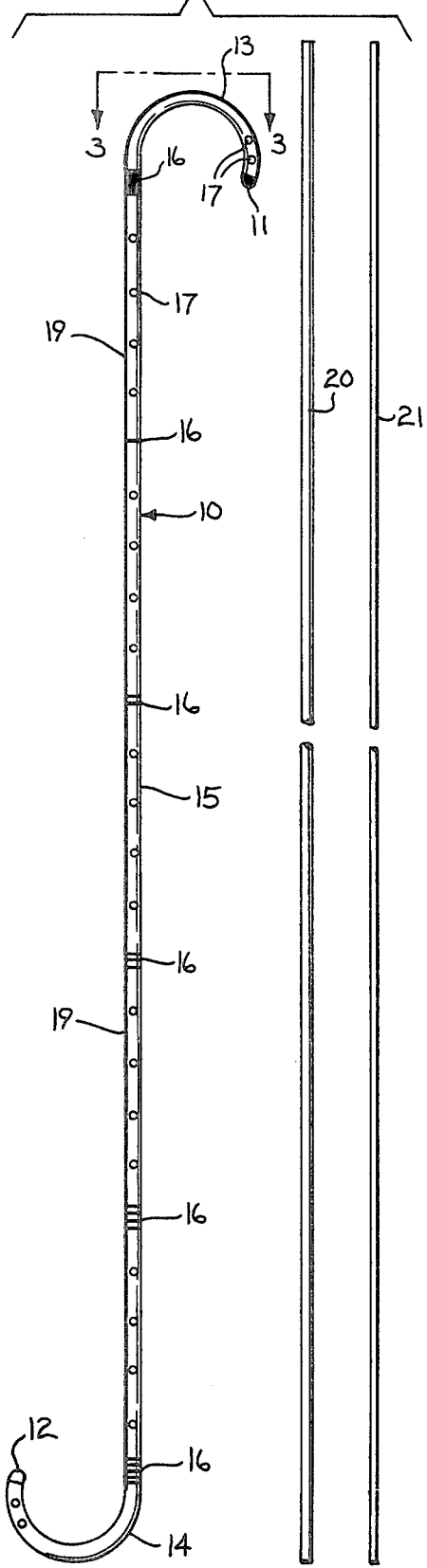
Fig. 1
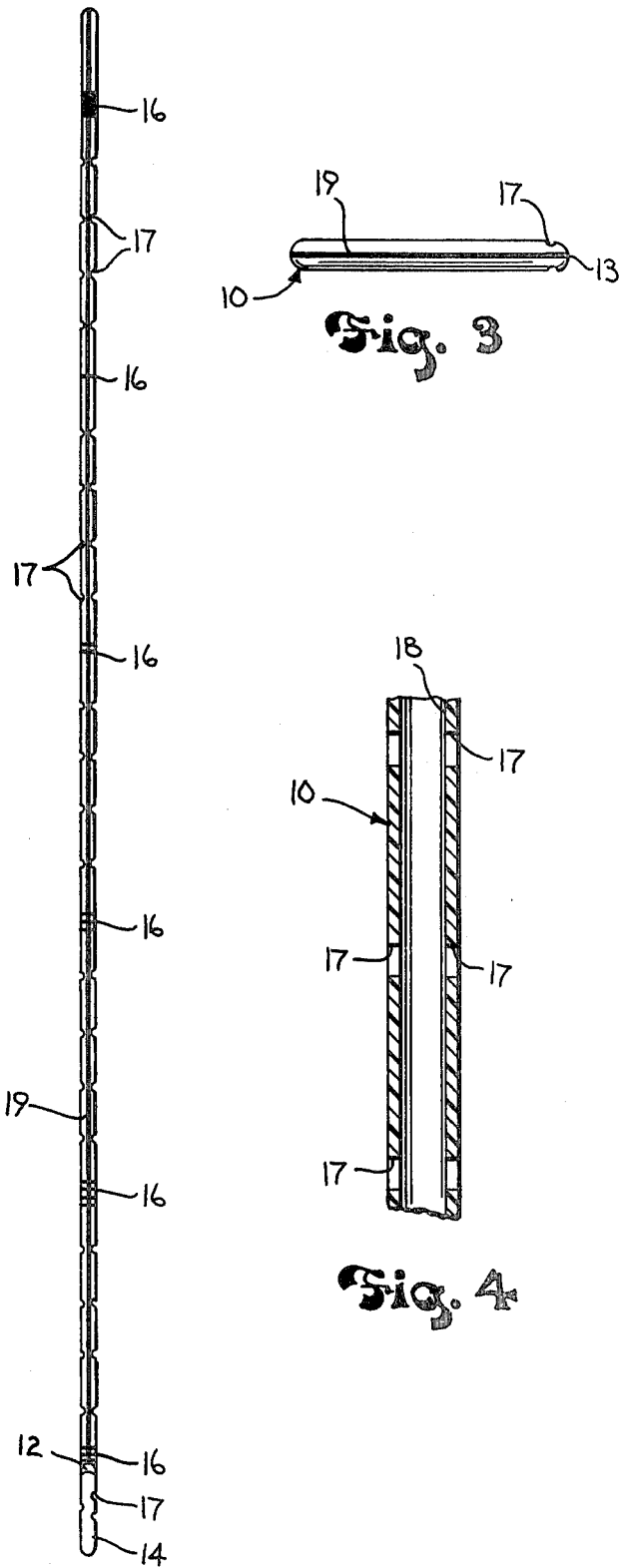
Fig. 2
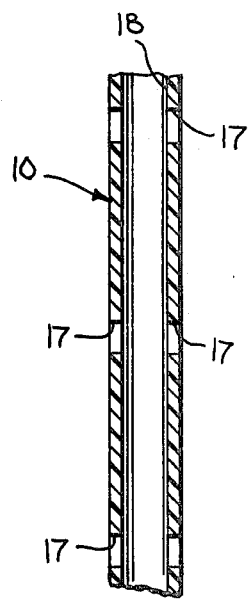
Fig. 3
Fig. 4

URETHERAL CATHETER STENT

BACKGROUND OF THE INVENTION

Indwelling ureteral catheter stents or drainage tubes have been used to bypass uretheral obstructions or ureterovaginal fistulas and maintain urinary drainage. In the past, stents made of open end silicone tubing have been used for this purpose and have provided good drainage for sustained periods of time. However, the use of such open end tubing has not been completely satisfactory. For example, in some instances, the tubing has migrated and in others it has been expelled.

Various attempts have been made to produce stents which do not have the problems which accompany the use of open end tubing. For example, stents have been designed which are closed at one end to facilitate passage into a body passage and which have at the other end a flange to make upward migration of the stent less likely. Another approach has been to provide the body of the stent with sharply pointed barbs which are designed to prevent downward migration and expulsion. However, such barbs increase the diameter of the stent making it more difficult to insert and in some instances can cause the stent to migrate outside the bladder to create medical or other problems for the urologist. Recently, a stent has been introduced which is made of stiff polyethylene. It has a relatively small flange on the distal end which is intended to prevent upward migration, and the proximal end is formed in the shape of a pigtail. Unfortunately, this stent must be introduced by the relatively complex Seldinger technique. Furthermore, the relatively small flange has not always prevented the stent from passing above the bladder making removal uncertain.

All the prior art stents have one feature in common: they are primarily designed to be passed endoscopically in a retrograde fashion and not during open surgery.

The ideal ureteral stent should have at least the following desirable characteristics: (1) the stent should be made of a material which is soft, quite flexible and resists tissue reaction and encrustation; (2) it should be radiopaque; (3) to facilitate its passage it should be of a uniform diameter throughout without barbs or flanges; (4) it should be easily passed during open surgery as well as endoscopically; (5) it should have means to prevent migration in either direction; and (6) it should be able to withstand repeated sterilization.

SUMMARY OF THE INVENTION

It is the general object of the present invention to disclose a ureteral catheter stent which is easily introduced both endoscopically and during open surgery, and which once in place resists migration.

It is a further object to disclose a stent which is of a soft, flexible, tissue compatible, radiopaque material which can withstand repeated sterilization, such as by autoclaving.

The ureteral catheter stent of the present invention comprises an elongated, flexible tubular member of uniform outside diameter throughout its length which has a proximal end which is curved gently and set in the form of a hook. Openings extend through the wall of the member to provide passages for fluid to enter the lumen of the tubular member and the proximal end of the member is closed to facilitate its introduction into a body passage. Since the stent is straightened for introduction into a body passage by inserting a wire stylet in the lumen of the stent, the stent is provided with indicating means which can be seen through a cystoscope and which will show the direction the proximal hook will extend when the stylet is removed so that proper placement is insured.

In the preferred embodiment, the stent is a tube of silicone elastomer which contains a radiopaque material and has a durometer of about 70 Shore 'A'. The proximal and distal ends of the tube are both closed and permanently set in the form of gently curved opposed hooks. The stent includes indicating means in the form of an index strip which is imprinted on the side of the tube opposite the proximal hook so that when the wire style is inserted into the stent to straighten the hook, it can be determined what direction the hook will form once the stylet is removed. In addition, the straight intermediate section of the preferred stent is provided with measurement markings every five centimeters.

The two gently formed opposed hooks of the stent prevent it from migrating either upwardly or downwardly once it is in place. Means for increasing the rigidity of the proximal and distal hooks may be incorporated. Plastic, fabric, metal or other suitable material may be incorporated into the hooks to make them less flexible and therefore make them more resistant to migration. The hooks extend in opposite directions so that when used as an indwelling ureteral stent the proximal end can hook into the lower calix or renal pelvis while the distal end curves out into the bladder. This design also prevents the tip of the stent from impinging directly into the bladder mucosa thereby decreasing discomfort and inflammation. These and still other objects and advantages of the invention will be apparent from the description which follows.

BRIEF DESCRIPTION OF THE DRAWINGS

FIG. 1 is a perspective view of the stent of the present invention and means for inserting the stent;

FIG. 2 is a back elevational view of the stent of FIG. 1;

FIG. 3 is a top plan view of the stent of FIG. 1; and

FIG. 4 is an enlarged sectional view of the stent seen in FIG. 1.

DESCRIPTION OF THE PREFERRED EMBODIMENT

In the preferred embodiment shown in FIG. 1, the stent 10 is seen to be an elongated tubular member which is closed at both ends 11 and 12. Portions adjacent each end are formed and set in the shape of gently curved hooks 13 and 14 which extend in opposite directions. A relatively straight intermediate section 15 extends between the opposed hooks 13 and 14. The section 15 is provided with measurement markings 16, which are preferably spaced 5 centimeters apart. The stent 10 is supplied in 7 French and 8.5 French sizes having an ID. of about 0.043 inches in 16, 24, 26, 28 and 30 cm lengths. The listed length of the stent 10 is the length of the section 15 and does not include the hooked ends 13 and 14. This allows the user to radiographically estimate the ureteral length and select the proper stent for passage.

Referring now to FIGS. 1 and 2, it can be seen that drainage openings 17 are located about a centimeter apart on both sides of the straight section 15. The openings 17 of the sides are preferably aligned. Returning to FIG. 1, it can be seen that there are similar openings 17 in the wall of the hooks 13 and 14.

As seen best in FIGS. 2 and 3, the back of the stent 10 bears an index stripe 19 which extends from the tip 11 of the proximal hook 13 past the last marking 16. The index stripe 19 is imprinted on the back wall of stent 10 and it serves as indicating means which can be seen through the optics of the cystoscope so that the user can see the direction that the proximal hook 13 and distal hook 14 will form when a straightening metal stylet is removed from the stent 10.

Returning to FIG. 1, there also can be seen a stent pusher 20 and a wire stylet 21 which may be used to help position the stent 10 in a body passage.

The preferred stent 10 is supplied with both ends 11 and 12 closed. As seen in FIG. 1, the proximal end 11 is preferably closed with a colored or opaque material and the distal end 12 with a clear material. When used for endoscopic insertion, the distal end 12 is clipped and the stylet wire 21 is introduced into the lumen 18 of the stent and passed through the full length of the stent 10 to straighten both hooks 13 and 14. The stent pusher 20 will normally be supplied in a ureteral catheter stent kit. However, a satisfactory stent pusher 20 may be made from a half length of a standard 5 F ureteral catheter. The stent pusher 20 is threaded over the stylet wire 21 and inserted 102 mm into the open end of the stent 10. This allows the partial withdrawal and redirection of the stent, if necessary, during standard retrograde catheterization. The index stripe 19 informs the use of the direction the proximal hook 13 will extend when the stylet 21 is removed. If necessary, the obstructed ureter is dilated with a standard catheter before inserting the stent 10. Once the stent 10 is properly positioned, the stylet 21 and stent pusher 20 are removed by withdrawing the stent pusher 20 while holding the stylet wire 21 causing the stent 10 and stent pusher 20 to disengage after which the stylet wire 21 and then the stent pusher 20 are withdrawn.

As the stent is of a uniform diameter with both ends smoothly closed and without flanges or barbs or other protrusions it also may be passed easily during open surgery through a pyelotomy, ureterotomy or transvesically as indicated. When the stent 10 is thus used, the distal end 12 is not clipped. Instead, the stylet 21 is inserted through a drainage hole 17 into the lumen 18 and used to straighten an appropriate length of the stent 10 and a hook 13 or 14. The stent 10 is then easily passed. Once the stylet 21 is withdrawn, the hook once again forms to prevent migration. This same technique is used to pass the stent 10 into the opposite viscus.

When it is desired to remove the stent 10, it may be removed endoscopically on an outpatient basis using either a foreign body or biopsy forceps or by using a stylet wire with a small hook formed at its end. In any case, once the stent is engaged, it is best removed by withdrawing the entire cystoscope.

The ureteral catherter stent 10 of the present invention is preferably made of silicone elastomer, preferably of the addition-reaction type, which when cured has a durometer of about 70 Shore 'A'. A suitable material is Dow Corning Silicone No. 4772 to which 10% barium sulfate has been added as a radiopaque material. Other plastic materials which resist incrustation with urine salts can also be used.

The stent is preferably formed by extruding uncured tubing of the desired size of a suitable silicone elastomer having the desired durometer. A suitable length of tubing is then placed in a form to retain the end portions of the tubing in the shape of gently curved hooks. The thus formed tubing is then cured by heating and the ends closed with silicone. The measurement markings 16 and index stripe 19 may be painted on or otherwise applied and, if desired, then covered with silicone to lock them in place. The drainage openings 17 may be formed by piercing the wall of the tubing with a flattened, sharpened hole cutter of the desired size or by use of a laser or any other conventional means.

The ureteral catheter stent may be supplied in a kit which contains one or an assortment of stents of different sizes and also includes a stylet wire and a stent pusher. In addition, if desired, an open end stent could be included for endoscopic use eliminating the need for the user to clip the distal end.

In the preferred embodiment described and shown in the drawing, the proximal and distal end portions of the catheter stent are both in the form of a gently curved hook. However, it is to be understood that the term "hook" is intended to include other functionally equivalent shapes which prevent migration and do not increase the effective outer diameter of the stent, or complicate its method of introduction.

It will be readily apparent to those skilled in the art that a number of modifications and changes can be made without departing from the spirit of the invention. For example, if desired, the stent could be made of a material other than silicone which provided the advantages of silicone elastomer. Obviously, the stent, although described as ureteral stent, also can be used in other applications than those described in the specification. Therefore, it is to be understood that the scope of the invention is not to be measured by the description, but only the claims that follow.

I claim:

1. An ureteral catheter stent comprises an elongated relatively flexible tubular member having at least one drainage opening extending through a wall thereof, the end portions of said tubular member are in the form of hooks, at least one of which has a closed end and the tubular member includes indicating means which indicate when the end portion is forcibly straightened the direction the closed end hook will extend when the portion is allowed to resume its normal shape.

2. The stent of claim 1 in which the tubular member is of substantially uniform outer diameter throughout its length.

3. The stent of claim 1 in which the tubular member is of a silicone elastomer material.

4. The stent of claim 1 in which both end portions have closed ends.

5. The stent of claim 1 in which the indicating means is an index stripe on the back of the hook portion having the closed end.

6. The stent of claim 1 in which the tubular member is of an unreinforced silicone elastomer having a durometer of about 70 Shore 'A'.

7. The stent of claim 1 in which the hook portions are reinforced to increase resistance to migration.

8. The stent of claim 1 in which the hook portions extend in opposite direction.

9. A kit for providing urinary drainage comprising:
(a) a wire stylet; and
(b) a ureteral catheter stent comprising an elongated relatively flexible tubular member having at least one drainage opening extending through a wall thereof, said member having end portions set in the form of hooks at least one of which has a closed end, and indicating means associated with said member which indicates when the wire stylet is in lumen of the tubular member and the hook with the closed end is straightened which direction the hook will extend when the stylet is removed.

10. The kit of claim 9 in which the tubular member is comprised of silicone elastomer having a durometer of about 70.

11. The kit of claim 9 in which both hook portions have closed ends.

12. The kit of claim 9 in which the hook portions extend in opposite directions.

13. The kit of claim 9 in which the stent is radiopaque to x-rays.

14. An indwelling ureteral catheter stent for use in maintaining urinary drainage in a patient, which stent compromises an elongated, flexible, tubular member having an internal lumen and an external wall of uniform outside diameter throughout its entire length, said member having a proximal end which is closed and set in the form of a hook, a relatively long straight intermediate section and a distal end which is also set in the form of a hook, said member having openings extending through its wall to provide a passage for fluid into the lumen and at least one opening at the distal end through which a wire stylet can be inserted into the lumen to straighten the member including the hooks so that the member can be cytoscopically inserted and positioned within the patient and through which the stylet can be removed when the stent is properly positioned so that upon removal the hooks will reform and prevent the member from migrating.

* * * * *